United States Patent [19]
Akahane et al.

[11] Patent Number: 5,063,257
[45] Date of Patent: Nov. 5, 1991

[54] DENTAL GLASS IONOMER CEMENT COMPOSITIONS

[75] Inventors: Shoji Akahane, Higashikurume; Satoshi Tosaki, Omiya; Yukiharu Kusayanagi, Tokyo; Shigenobu Kusakai, Tokyo; Kazuo Hirota, Tokyo; Kentaro Tomioka, Chofu, all of Japan

[73] Assignee: G-C Dental Industrial Corp., Tokyo, Japan

[21] Appl. No.: 448,298

[22] Filed: Dec. 11, 1989

[30] Foreign Application Priority Data

Dec. 16, 1988 [JP] Japan .................. 63-316303

[51] Int. Cl.$^5$ .......................... C08F 2/50; A61K 6/08
[52] U.S. Cl. ......................... 523/116; 523/115; 523/117; 522/13; 522/14; 522/21; 522/24; 522/77; 522/83; 522/95; 522/96; 522/120; 522/121; 522/908
[58] Field of Search ............ 523/115, 116, 117; 522/13, 14, 21, 24, 77, 83, 95, 96, 120, 121, 908

[56] References Cited

U.S. PATENT DOCUMENTS 4,820,744 4/1989 Kubota et al. .................. 523/116

Primary Examiner—Paul R. Michl
Assistant Examiner—T. McDonald, Jr.
Attorney, Agent, or Firm—Oblon, Spivak, McClelland, Maier & Neustadt

[57] ABSTRACT

A dental glass ionomer cement composition comprises:
(a) 5 to 100 parts by weight of a polymer of an α-β unsaturated carboxylic acid having a weight average molecular weight of 5,000 to 40,000,
(b) 5 to 100 parts by weight of a fluoroaluminosilicate glass powder having an average particle size of 0.02 to 10 μm and a specific gravity of 2.4 to 4.0 and capable of reacting with said "polymer of an α-β unsaturated carboxylic acid having a weight average molecular weight of 5,000 to 40,000",
(c) 5 to 100 parts by weight of a polymerizable unsaturated organic compound having at least one $CH_2=C(R1)-COO-$ group wherein R1=H or $CH_3$,
(d) 0.01 to 5 parts by weight of a polymerization catalyst,
(e) 2 to 50 parts by weight of water,
(f) 0.01 to 20 parts by weight of a surface active agent, and
(g) 0.01 to 5 parts by weight of a reducing agent, and optionally h. 0 to 50 parts by weight of an inorganic filler having an average particle size of 0.02 to 10 μm and undergoing no reaction with said "polymer of an α-β unsaturated carboxylic acid having a weight average molecular weight of 5,000 to 40,000".

13 Claims, No Drawings

DENTAL GLASS IONOMER CEMENT COMPOSITIONS

BACKGROUND OF THE INVENTION

1. Field of the Invention

The present invention relates to a dental cement, particularly, to a dental glass ionomer cement. More particularly, the present invention is concerned with a dental glass ionomer cement composition designed to be simultaneously curable by polymerization.

2. Prior Art

Dental cements now available are of varied types and find wide applications, typically including a zinc phosphate cement making use of the reaction of zinc oxide with phosphoric acid, a polycarboxylate cement making use of the reaction of zinc oxide with a polycarboxylic acid, a zinc oxide eugenol cement making use of the reaction of zinc oxide with eugenol, a glass ionomer cement making use of the reaction of fluoroaluminosilicate glass powders with polycarboxylic acid and a resin cement making use of the polymerization of an acrylic base monomer.

As yet, any perfect and ideal dental cement is still unavailable, because such dental cements have their own merits and demerits. Referring to the demerits, the zinc phosphate cement is lacking in adhesion to tooth substance and tends to make phosphoric acid produce its own irritating action at the initial stage of setting; the polycarboxylate cement gives a hardened mass with a comparatively low final strength; the eugenol cement is not only of low strength and poor in intra-mouth durability so that its use is limited to temporal sealing and cementing, but also makes eugenol produce its own irritating action; and the resin cement is controversial in terms of biocompatibility.

Because of its merits such as improved biocompatibility, adhesion to tooth substance, satisfactory intra-oral durability and hardened mass having translucency and good appearance, on the other hand, the glass ionomer cement has now wide applications such as cementing of inlays, crowns and so on, filling of caries cavities, lining and preventive sealing of pits and fissures. However, the most serious problem with the glass ionomer cement is that when it is in touch with moisture such as saliva at the early stage of setting, its setting reaction is prevented from proceeding, ending up in deteriorations of the physical properties of the hardened mass.

The glass ionomer cement is obtained by the neutralizing reaction of a polycarboxylic acid (an acid) with fluoroaluminosilicate glass (a base) in the presence of water. Hence, that reaction is so readily affected by water that, upon coming into contact with water at the early stage of setting, its hardened mass is embrittled on its surface with a reduction in strength. At this time, the hardened mass clouds on its surface, offering an undesirable aesthetic problem. For improvements in glass ionomer cements, multiple attempts have been made up to date. For instance, Japanese Patent Publication Nos. 54-21858 and 57-2210 teach to make setting proceed rapidly by the addition of a chelating agent and a fluorocomplex, respectively. Never is any solution provided so far to this problem.

SUMMARY OF THE INVENTION

As a result of intesive studies made to solve the above problem, we have now found that a solution can be provided thereto by using a dental glass ionomer cement composition comprising:

(a) a polymer of an $\alpha$-$\beta$ unsaturated carboxylic acid having a weight average molecular weight of 5,000 to 40,000, (b) a fluoroaluminosilicate glass powder having a mean particle size of 0.02 to 10 $\mu$m and a specific gravity of 2.4 to 4.0 and capable of reacting with "(a) a polymer of an $\alpha$-$\beta$ unsaturated carboxylic acid having a weight average molecular weight of 5,000 to 40,000", (c) a polymerizable unsaturated organic compound containing at least one $CH_2=C(R1)-COO-$ group wherein $R1=H$ or $CH_3$, (d) a polymerization catalyst, (e) water (f) a surface active agent, and (g) a reducing agent.

With the above-described glass ionomer cement composition, setting can occur initially through the neutralizing reaction of the fluoroaluminosilicate glass powder with the polymer of an $\alpha$-$\beta$ unsaturated carboxylic acid concurring with the polymerizing reaction of the polymerizable component present therewith, whereby the initial setting reaction can proceed rapidly sufficient to obtain a glass ionomer cement much less sensitive to water at the initial stage of setting.

DETAILED EXPLANATION OF THE INVENTION

In the present invention, it is preferred that "(c) a polymerizable unsaturated organic compound containing at least one $CH_2=C(R1)-COO-$ group wherein $R1=H$ or $CH_3$" undergoes no reaction with [(b) a fluoroaluminosilicate glass powder having a mean particle size of 0.02 to 10 $\mu$m and a specific gravity of 2.4 to 4.0 and capable of reacting with "(a) a polymer of an $\alpha$-$\beta$ unsaturated carboxylic acid having a weight average molecular weight of 5,000 to 40,000"]. In other words, it is preferred for that compound not to contain an acid group reacting with the glass powder, for instance, a carboxylic acid ($-COOH$), a phosphorus-containing acid group ($-PO(OH)_2$, $-OPO(OH)_2$, $-PO(OH)OR$, $-OPO(OH)OR$ or the like), a sulfur-containing acid group ($-SO_2H$, $-SO_3H$, $-OSO_3H$ or the like) and a boron-containing acid group ($-B(OH)_2$, $-OB(OH)_2$, $-B(OH)OR$, $-OB(OH)OR$ or the like) or their salts. Again preferably, nor does the compound contain any other acid group undergoing an acid-base reaction with the glass powder.

According to a preferred aspect of the present invention, there is provided a dental glass ionomer cement composition comprising:

(a) 5 to 100 parts by weight of a polymer of an $\alpha$-$\beta$ unsaturated carboxylic acid having a weight average molecular weight of 5,000 to 40,000, (b) 5 to 100 parts by weight of a fluoroaluminosilicate glass powder having a mean particle size of 0.02 to 10 $\mu$m and a specific gravity of 2.4 to 4.0 and capable of reacting with "(a) a polymer of an $\alpha$-$\beta$ unsaturated carboxylic acid having a weight average molecular weight of 5,000 to 40,000", (c) 5 to 100 parts by weight of a polymerizable unsaturated organic compound containing at least one $CH_2=C(R1)-COO-$ group wherein $R1=H$ or $CH_3$, (d) 0.01 to 5 parts by weight of a polymerization catalyst, (e) 2 to 50 parts by weight of water (f) 0.01 to 10 parts by weight of a surface active agent, and (g) 0.01 to 5 parts by weight of a reducing agent.

With the glass ionomer cement composition according to this aspect, setting can again occur initially through the neutralizing reaction of the fluoroaluminosilicate glass powder with the polymer of an α-β unsaturated carboxylic acid concurring with the polymerizing reaction of the polymerizable component present therewith, whereby the initial setting reaction can proceed rapidly sufficient to obtain a glass ionomer cement much less sensitive to water at the initial stage of setting.

According to a further aspect of the present invention, [(b) a fluoroaluminosilicate glass powder having a mean particle size of 0.02 to 10 μm and a specific gravity of 2.4 to 4.0 and capable of reacting with "(a) a polymer of an α-β unsaturated carboxylic acid having a weight average molecular weight of 5,000 to 40,000"] is coated on its surface with an organic compound having a polymerizable, ethylenically unsaturated double bond in an amount of 0.01 to 20 parts by weight with respect to 100 parts by weight of said glass powder. Physical properties are further improved by said polymerizable, ethylenically unsaturated double bond remaining in said fluoroaluminosilicate glass powder.

According to a still further aspect of the present invention, the cement containing the aforesaid components is pasted so as to improve the mixing manipulatability of a dental glass ionomer cement.

By the "(a) a polymer of an α-β unsaturated carboxylic acid having a weight average molecular weight of 5,000 to 40,000" are meant polymers of α-β unsaturated mono- or di-carboxylic acids, for instance, homo- or co-polymers of acrylic, methacrylic, 2-chloroacrylic, 3-chloroacrylic, aconitic, mesaconic, maleic, itaconic, fumaric, glutaconic and citraconic acids. Such copolymers may be copolymers of α-β unsaturated carboxylic acids or an α-β unsaturated carboxylic acid with other component copolymerizable therewith. Preferred in this case is that the proportion of the α-β unsaturated carboxylic acid is 50% or more. By the "component copolymerizable therewith" are meant, for instance, acrylamide, acrylonitrile, methacrylate esters, acrylate esters, salts of acrylic acids, vinyl chloride, allyl chlorides and vinyl acetate. Of the polymers of α-β unsaturated carboxylic acids, particular preference is given to a homo- or co-polymer of acrylic or maleic acid. The use of a polymer having a weight average molecular weight 5,000 or less poses a durability problem, since the strength of a hardened composition is low. There is also a drop in adhesive strength to a tooth substance. Due to its too high consistency at the time of mixing, on the other hand, it is very hard to mix a glass ionomer cement composition with which a polymer having a weight average molecular weight exceeding 40,000 is used. Therefore, the weight average molecular weight of the α-β unsaturated carboxylic acid used in the present invention is limited to the range of 5,000 to 40,000. Preferably, such a polymer of the α-β unsaturated carboxylic acid is used in an amount of 5 to 100 parts by weight in the compositions according to the present invention. At less than 5 parts by weight, there may be a drop in adhesive strength to a tooth substance which is one of the features of glass ionomer cement. At higher than 100 parts by weight, on the other hand, there may be an increase in solubility of hardened masses, which leads to poor durability. Therefore, the polymer of the α-β unsaturated carboxylic acid preferably accounts for 5 to 100 parts by weight of the total compositions according to the present invention.

Any particular limitation is not imposed upon the fluoroaluminosilicate glass powder used in the present invention, provided that it has a mean particle size of 0.02 to 10 μm and a specific gravity of 2.4 to 4.0 and is capable of reacting with "(a) a polymer of an α-β unsaturated carboxylic acid having a weight average molecular weight of 5,000 to 40,000". According to the present invention, the glass powder has its mean particle size ranging from 0.02 to 10 μm. At a mean particle size exceeding 10 μm, no surface smoothness of hardened mass is obtained by polishing, thus giving an ill feeling of contact in the oral cavity. Additionally, a setting reaction with a liquid is unfavorably delayed. When a powder as fine as expressed in terms of a mean particle size less than 0.02 μm is used, on the other hand, it is hardly available in view of absolute quantity that physical properties deteriorate. It is understood that the particle size may be determined by ordinary means and is expressed in terms of the average of the major and minor diameters of a particle. According to the present invention, the glass powder has its true specific gravity ranging from 2.4 to 4.0. The true specific gravity of glass powders may be determined with a specific gravity bottle, etc. in ordinary manners. If the true specific gravity departs from such a range, then the reactivity of the glass used according to the present invention drops and has an adverse influence upon physical properties.

The glass powder used according to the present invention will now be explained in further detail. Preferable to this end is an aluminosilicate glass containing as the main components $Al^{3+}$, $Si^{4+}$, $F^-$, $O^{2-}$ and $Ca^{2+}$ and/or $Sr^{2+}$. Referring to the proportion of such main components, it is particularly preferred that of the total weight of glass, $Al^{3+}$ accounts for 10 to 21% by weight; $Si^{4+}$ 9 to 24% by weight; $F^-$ 1 to 20% by weight; and $Sr^{2+}$ plus $Ca^{2+}$ 10 to 34% by weight. The proportion of these main ingredients has a great deal of influence on manipulatability and physical properties such as setting rate, final strength and solubility. When the proportion of $Al^{3+}$ is 10% or less by weight, the setting reaction is slow and the strength of hardened mass is low, on the other hand the proportion of $Al^{3+}$ is 21% or more by weight, difficulty is involved in the preparation of glass. Even if glass is prepared one way or another, it is then of reduced transparency and looks not good to look at. When the proportion of $Si^{4+}$ is 9% or less by weight, it is again difficult to prepare glass. A proportion of $Si^{4+}$ exceeding 24% by weight is not practical, since the rate of setting is delayed. Another problem arises in connection with durability because of reduced strength. A proportion of $F^-$ less than 1% by weight is not practical, since it is then hard to use and manipulate cement due to absence of allowance in time to mix cement. A proportion of $F^-$ exceeding 20% by weight increases the length of final setting time and solubility in water, making durability poor. A proportion of $Sr^{2+}$ plus $Ca^{2+}$ is 10% or less by weight fails to make setting sharp, resulting in an increase in the length of setting time. Moreover, it is difficult to prepare glass. A proportion of $Sr^{2+}$ plus $Ca^{2+}$ exceeding 34% by weight is in fact difficult to apply, since setting is too fast to take sufficient time for manipulation. There is also an increase in solubility in water, thus posing a durability problem.

For the reasons set forth above, the proportion of the main components in glass is most preferably limited to such a range as defined above. The fluoroaluminosilicate glass used in the present invention may be prepared by known glassmaking processes. For instance, a glass material may be selected from silica, alumina, aluminium hydroxide, aluminium silicate, mullite, calcium silicate, strontium silicate, sodium silicate, aluminium carbonate, calcium carbonate, strontium carbonate, sodium carbonate, sodium fluoride, calcium fluoride, aluminium fluoride, strontium fluoride, aluminium phosphate, calcium phosphate, strontium phosphate, sodium phosphate and so on, and are weighed out. Then, the raw material may be melted at a high temperature of 1,000° C. or above for melting, cooled down and ground. Preferably, the fluoroaluminosilicate glass powder accounts for 5 to 100 parts by weight of the compositions of the present invention. At 5 or less parts by weight, the physical properties of hardened masses deteriorate, whereas at 100 or more parts by weight, there is a drop in reactivity.

The fluoroaluminosilicate glass powders may be used in combination with a known inorganic filler widely used which is the so-called dental composite resins. By the "inorganic filler" are meant [(h) an inorganic filler having a mean particle size of 0.02 to 10 μm and undergoing no reaction with "(a) a polymer of an α-β unsaturated carboxylic acid having a weight average molecular weight of 5,000 to 40,000"]. The inorganic filler may include, e.g., quartz, colloidal silica, feldspar, alumina, strontium glass, barium glass, borosilicate glass, kaolin, talc, calcium carbonate, calcium phosphate, titania and barium sulfate. Use may also be made of a composite filler obtained by the grinding of an inorganic filler-containing polymer. Of course, they may be mixed together for use.

It is understood that the present invention does not exclude the use of such an organic filler as polymethyl acrylate and methacrylate, polyethyl acrylate and methacrylate and copolymers of ethylene with vinyl acetate, which may optionally be mixed with the inorganic filler for use.

By the "(c) a polymerizable unsaturated organic compound having at least one $CH_2=C(R1)$—COO—group wherein R1=H or $CH_3$" is meant a polymerizable unsaturated organic compound having an acryloyl or methacryloyl group, which preferably undergoes no reaction with the fluoroaluminosilicate glass powders according to the present invention. Preference is given to, inter alia, an ester of acrylic or methacrylic acid. Examples are methyl methacrylate, methyl acrylate, ethyl methacrylate, ethyl acrylate, propyl methacrylate, propyl acrylate, isopropyl methacrylate, isopropyl acrylate, hydroxymethyl methacrylate, hydroxymethyl acrylate, hydroxyethyl methacrylate, hydroxyethyl acrylate, hydroxypropyl methacrylate, hydroxypropyl acrylate, tetrahydrofurfuryl methacrylate, tetrahydrofurfuryl acrylate, glycidyl methacrylate, glycidyl acrylate, triethylene glycol dimethacrylate, triethylene glycol diacrylate, tetraethylene glycol dimethacrylate, tetraethylene glycol diacrylate, trimethylolethane trimethacrylate, trimethylolpropane trimethacrylate, pentaerythritol trimethacrylate, trimethylolethane triacrylate, trimethylolpropane triacrylate, pentaerythritol triacrylate, pentaerythritol tetramethacrylate, pentaerythritol tetra-acrylate, ethylene dimethacrylate, ethylene diacrylate, ethylene glycol dimethacrylate, ethylene glycol diacrylate, buthylene glycol dimethacrylate, buthylene glycol diacrylate, neopentyl glycol dimethacrylate, neopentyl glycol diacrylate, 1,3-butanediol dimethacrylate, 1,3-butanediol diacrylate, 1,4-butanediol dimethacrylate, 1,4-butanediol diacrylate, 1,6-hexanediol dimethacrylate, 1,6-hexanediol diacrylate, di-2-methacryloxyethyl-hexametylene dicarbamate, di-2-methacryloxyethyl-trimethylhexametylene dicarbamate, di-2-methacryloxyethyl-dimethylbenzene dicarbamate, di-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-b 1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'-bis(4-acryloxyphenyl)propane, 2,2'-bis[4(2-hydroxy-3-methacryloxyphenyl)]propane, 2,2'-bis[4(2-hydroxy-3-acryloxyphenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane and so on.

As exemplified above, a number of methacrylates or acrylates may be used. Needless to say, they may be used alone or in combination with two or more. It is understood that the present invention is not necessarily limited to such methacrylates and acrylates, and analogues thereto may be used alike. On the other hand, such polymerizable unsaturated organic compounds containing at least one $CH_2=C(R1)$—COO—group wherein R1 stands for H or $CH_3$ may be used in combination with a polymerizable organic compound such as styrene, N-vinylpyrrolidone and divinylbenzene. Of the polymerizable unsaturated organic compounds containing at least one $CH_2=C(R1)$—COO—group wherein R1 stands for H or $CH_3$, more preferable are 2,2'-bis[3(4-phenoxy)-2-hydroxypropane-1-methacrylate]propane, 2,2'-bis[3(4-phenoxy)-2-hydroxypropane-1-acrylate]propane, 1-hydroxy-1-naphthoxy-3-methacrylate, 2,2'-bis(4-methacryloxyphenyl)propane, 2,2'-bis(4- acryloxyphenyl)propane, 2,2'-bis(4-methacryloxyethoxyphenyl)propane, neopentyl glycol dimethacrylate, triethylene glycol dimethacrylate, di-2-methacryloxyethyl-hexamethylene dicarbamate, di-2-methacryloxyethyl-trimethylhexamethylene dicarbamate, di-2-methacryloxyethyl-dimethylbenzene dicarbamate, di-2-methacryloxyethyl-dimethylcyclohexane dicarbamate, methylene-bis-2-methacryloxyethyl-4 -cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzen dicarbamate, di-1-chloromethyl-2-methacryloxyethyl-dimethylcyclohexane dicarbomate, methylene-bis-1-chloromethyl-2-methacryloxyethyl-4-cyclohexyl carbamate and so on.

On the other hand, such numerous esters of acrylic and methacrylic acids are not necessarily limited to one, and may be used in combination with two or more. Most preferably, urethane, epoxy and polyol methacrylates account for 50% or more of the total weight of the "(c) a polymerizable unsaturated organic compound containing at least one $CH_2=C(R1)-COO-$ group wherein R1 stands for H or $CH_3$". The urethane methacrylate is a general term applied to methacrylate esters having an urethane skeleton, and refers to, e.g., such carbamate compounds as mentioned above. The polyol methacrylate refers to an ester of a di- or more-valent alcohol with methacrylic acid. The epoxy methacrylate is a general term applied to methacrylate esters obtained by the reaction of epoxy compounds with acrylate or methacrylate esters. In the compositions of the present invention, the amount of the "(c) a polymerizable unsaturated organic compound containing at least one $CH_2=C(R1)-COO-$ group wherein R1 stands for H or $CH_3$" is preferably in a range of 5 to 100 parts by weight. At 5 or less parts by weight, the initial setting properties that characterizes the present invention deteriorate whereas, at 100 or more parts by weight, there is a drop in adhesion to tooth substance.

The polymerization catalysts will now be referred to.

The polymerization of such polymerizable unsaturated organic compounds may be initiated with various polymerization initiators. It is usually practical, however, to use a so-called redox reaction with redox catalysts or a photopolymerizing reaction with photopolymerization initiators. In view of manipulatability in particular, the photopolymerizing reaction is superior. Catalysts used to this end may be those heretofore known in the art. Among others, carbonylic photopolymerization initiators are preferred. Preferable are, for instance, adjacent polyketone compounds such as benzyl, p,p'-dimethoxybenzyl, p,p'-dichlorobenzyl and camphor quinone, α-carbonyl alcohols such as benzoin and α-alkylbenzoin, ketal compounds such as benzyl dimethyl ketal, benzyl diethyl ketal, benzyl (2-methoxyethyl)ketal, 4,4'-dimethylbenzyl-dimethyl ketal, benzoin alkyl ether compounds, acetophenone derivatives, acylphosphine oxides, polynuclear quinone compounds such as α-naphtyl, acenaphtyl and anthraquinone, thioxanthone compounds such as thioxanthone, 2-chlorothioxanthone, 2,4-diethoxythioxanthone and methylthioxanthone. In some cases, such photopolymerization initiators may be used in combination with two or more.

The polymerization catalysts may preferably be used in an amount ranging from 0.01 to 5 parts by weight with respect to the compositions of the present invention. At 0.01 or less parts by weight, any sharp initial curing cannot be obtained. At 5 or more parts by weight, no noticeable effect may be attained in some cases.

Such photopolymerization initiators may be used in combination with a reducing agent to make the curing sharper proceed more rapidly. The reducing agents to be used, although not particularly specified, may be amines that are generally known in the art, for instance, an amine disclosed in Japanese Patent Application No. 60(1985)-199385. The reducing agents most preferably used in the present invention include dimethylaminoethyl methacrylate, n-butylamine, triethylamine, triethyl-n-butylphosphine, 4-dimethylaminomethyl benzoate, 4-dimethlaminoethyl benzoate, 4-dimethylaminoisoamyl benzoate and so on. The reducing agent is used in an amount ranging from 0.01 to 5 parts by weight with respect to the compositions of the present invention. An amount exceeding 5 parts by weight is not desirable, since hardness masses may then discolor.

The glass ionomer cement compositions of the present invention may optionally contain polymerization inhibitors, UV absorbers and organic peroxides that are usually employed at need.

In the present invention, use may be further made of a polybasic carboxylic acid disclosed in Japanese Patent Application No. 51(1976)-18480. In some cases, the addition of the polybasic carboxylic acid may result in an increase in the strength of the final hardened masses.

A component essentially inevitable for the dental glass ionomer cement compositions of the present invention is water. The reason is that the reaction of the aluminosilicate glass with the polymer of an α-β unsaturated carboxylic acid proceeds in the presence of water. Where water exists, the dental glass ionomer cement compositions of the present invention also bond to the surface of teeth. Thus, the compositions of the present invention always contain water in an amount ranging preferably from 2 to 50 parts by weight. At 50 or more parts by weight, the physical properties of hardened masses may drop whereas, at 2 or less parts by weight, there is a drop in such adhesion to tooth substance that characterizes glass ionomer cement.

In the present invention, the surface active agent should be used. That is, the "(c) a polymerizable unsaturated organic compound having at least one $CH_2=C(R1)-COO-$ group wherein $R1=H$ or $CH_3$" is in most cases not miscible with water and so should be uniformly mixed and emulsified with water or an aqueous solution by the surface active agent. In this manner, multi-component compositions similar to those according to the present invention are more stabilized in terms of storability and physical properties. In the present invention, use may be made of any surfactant which is capable of forming an emulsion. Examples are sorbitan fatty acid esters, glycerin fatty acid esters, decaglycerin fatty acid esters, diglycerin fatty acid esters, tetraglycerin fatty acid esters, diglycerin fatty acid esters, tetraglycerin fatty acid esters, hexaglycerin fatty acid esters, propylene glycol fatty acid esters, pentaerythritol fatty acid esters, polyoxyethylene sorbitan fatty acid esters, polyoxysorbitol fatty acid esters, polyoxyethyleneglycerin fatty acid esters, polyoxyethylenealkyl ether, polyoxyethylene phytosterols, polyoxyethylene phytostanols, polyoxyethylene alkyl ethers, polyoxyethylene alkylphenyl ether, polyoxyethylene castor oil, polyoxyethylene hardened castor oil, polyoxyethylene lanorin, polyoxyethylene lanorin alcohols, polyoxythylene beeswax derivatives, polyoxyethylenealkylamine, polyoxyethylene fatty amides, polyoxyethylene alkylphenyl formaldehyde condensates, alkyl sulfates, lecithin, polyoxyethylene alkyl ether acetates, alkyl ether carboxylates, alkyl sulfocarboxylates, $\alpha$-olefin sulfonates, alkyl phosphates, polyoxyethylene alkyl ether phosphates and aliphatic amines. These surface active agents may be optionally selected and used in combination.

Additionally, the present invention includes the surface-treatment of the fluoroaluminosilicate glass powder with the organic compound having a polymerizable, ethylenically unsaturated double bond. In some cases, this treatment may results in an increase in the final strength of hardened masses, thus making a contribution to the intra-oral stabilization of cement. Preferably, the fluoroaluminosilicate glass is coated on its surface with the organic compound having a polymerizable, ethylenically unsaturated double bond in a quantity of 0.01 to 20 parts by weight of the latter with respect to 100 parts by weight of the former. In most cases, considerable improvements in physical properties are achievable in such a range. The unsaturated organic compound having a polymerizable, ethylenical double bond, used for the treatment of the glass powders in the present invention, is understood to include, e.g., vinylic silane coupling agents such as vinyltrimethoxysilane, vinyltriethoxysilane, $\gamma$-methacryloxypropyltrimethoxysilane, $\gamma$-methacryloxypropylmethyldimethoxysilane, vinyltrichlorosilane and vinyl-tris(2-methoxyethoxy)silane, unsaturated carboxylic acids such as methacrylic acid, acrylic acid and maleic acid. Of importance in this connection is that the ethylenical double bond remains after the treatment. The fluoroaluminosilicate glass powder may be treated on its surface with the organic compound having a polymerizable, ethylenical double bond in known manners. For instance, after dissolved or suspended in a suitable solvent, the "organic compound having a polymerizable, ethylenically unsaturated double bond" may be mixed with the aluminosilicate glass for reaction with its surface. Subsequent drying can give a glass powder treated on its surface as desired. Most preferable for the present invention are the silane coupling agents.

On the other hand, the dental glass ionomer cement compositions of the present invention may be considered to be in various forms. Mentioned are, for instance, powder/liquid, paste/liquid and paste/paste. While such forms have their own merits and demerits, preference is given to the paste type in view of manipulatability. In any form, it is difficult in terms of storability to make co-exist the three components concurrently in one form, i.e., the $\alpha$-$\beta$ unsaturated carboxylic copolymer, the fluoroaluminosilicate glass and water. Reference will now be made to the specific forms. For the powder/liquid form, an aqueous solution of the $\alpha$-$\beta$ unsaturated carboxylic acid, in which is emulsified the polymerizable unsaturated organic compound having at least one $CH_2=C(R1)$—COO—group wherein R1 = H or $CH_3$, is basically added to the aluminosilicate glass powders. Needless to say, the $\alpha$-$\beta$ unsaturated carboxylic acid may be powderized for addition to the powder component. For the paste/liquid form, the powders in the powder and liquid forms may be pasted. For the paste/paste type, the components may almost freely be distributed to the two components. For instance, a paste including the fluoroaluminosilicate glass powders may additionally contain the polymerizable unsaturated organic compound having at least one $CH_2=C(R1)$—COO—group wherein R1 = H or $CH_3$. In this case, it is preferable that such a paste is combined with another paste containing as the main component an aqueous solution of the $\alpha$-$\beta$ unsaturated carboxylic acid polymer. Further, the fluoroaluminosilicate glass powders may be pasted with an aqueous solution of a high-molecular substance. Still further, such a paste may be emulsified and mixed with the fluoroaluminosilicate glass powders may additionally contain the polymerizable unsaturated organic compound having at least one $CH_2=C(R1)$—COO—group wherein R1 = H or $CH_3$. In those cases, it is preferable that another paste contains as the main component an aqueous solution of the $\alpha$-$\beta$ carboxylic acid polymer. For pasting, a water-soluble high-molecular substance may be used auxiliarily. The water-soluble high-molecular substances suitably used for this purpose may be starch, starch derivatives, various cellulosic derivatives such as carboxymethyl cellulose, methyl cellulose, hydroxyethyl cellulose, hydroxypropyl cellulose and phthal acetate cellulose, cellulose derivative salt, soda polyacrylate, cross-linked type polyacrylates, polyvinyl alcohols, polyethylene glycols, polyethylene oxides, polyvinylpyrrolidone, polyacrylamides, polyethyleneimines, alginates, alginic derivatives, Carrageenan, Cyamoposis gum, tragacanth gum, xanthane gum, Locust bean gum and chitin derivatives. In use, such water-soluble high-molecular materials are preferably in a quantity range of 0 to 20 parts by weight. It is preferred in the present invention that the paste has a viscosity of 2000 cP or higher, since manipulatability of mixing is then superior.

EXAMPLES

The present invention will now be explained more specifically with reference to the following examples.

EXAMPLE 1

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 100 g of the glass powders was 1 g of camphor quinone, and they were fully mixed together with a mortar in a dark room to prepare cement powders. On the other hand, 30 g of polyacrylic acid having an average molecular weight of 20,000, 20 g of di-2-methacryloxyethyl-hexamethylene dicarbamate, 50 g of distilled water and 3 g of polyethylene glycol laurate ester were mixed under agitation for 60 minutes into a homogeneous state to prepare an aqueous cement solution. 2.5 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 23 Hv in measurement. A compressive strength showed 140 MPa after one day. To put it another way, the glass ionomer cement composition of this invention can be said to show so much sharpness at initial setting, to be much less sensitive to water at the early stage of setting and thus stable in the oral cavity.

EXAMPLE 2

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 100 g of the glass powders were 0.5 g of camphor quinone and 1.0 g of dimethylaminoethyl methacrylate, and they were well-mixed together with a mortar in a dark room to prepare cement powders. On the other hand, 30 g of polyacrylic acid having an average molecular weight of 18,000, 20 g of di-2-methacryloxyethyl-hexamethylene dicarbamate, 50 g of distilled water and 3 g of polyethylene glycol laurate ester were mixed under agitation for 60 minutes into a homogeneous state to prepare an aqueous cement solution. 2.5 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 23 Hv in measurement. A compressive strength showed 140 MPa after one day. To put it another way, the glass ionomer cement composition of this invention can be said to show so much sharpness at initial setting, to be much less sensitive to water at the early stage of setting and thus stable in the oral cavity.

EXAMPLE 3

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 100 g of the glass powders were 1.0 g of benzyl dimethyl ketal, 0.2 g of 1,2-benzanthraquinone and 0.5 g of dimethylaminoethyl methacrylate, and they were fully mixed together with a mortar in a dark room to prepare cement powders. On the other hand, 25 g of polyacrylic acid having an average molecular weight of 18,000, 5 g of tartaric acid, 30 g of di-2-methacryloxyethylhexamethylene dicarbamate, 40 g of distilled water and 2 g of polyoxyethylene sorbitol monolaurate ester were mixed under agitation for 60 minutes into a homogeneous state to prepare an aqueous cement solution. 2.5 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 24 Hv in measurement. A compressive strength showed 145 MPa after one day. To put it another way, the glass ionomer cement composition of this invention can be said to show so much sharpness at initial setting, to be much less sensitive to water at the early stage of setting and thus stable in the oral cavity.

EXAMPLE 4

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 100 g of the glass powders were 0.5 g of camphor quinone, 0.5 g of benzoyl peroxide and 0.5 g of 4-dimethylaminoisoamyl benzoate, and they were well-mixed together with a mortar in a dark room to prepare cement powders. On the other hand, 30 g of polyacrylic acid having an average molecular weight of 40,000, 30 g of di-1-methyl-2-methacryloxyethyl-tirmethylhexamethylene dicarbamate, 40 g of distilled water, 1.5 g of polyoxyethylene sorbitol monolaurate ester and 0.5 g of decaglycerin monostearate ester were mixed under agitation for 60 minutes into a homogeneous state to prepare an aqueous cement solution. 2.5 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 22 Hv in measurement. A compressive strength showed 139 MPa after one day. To put it another way, the glass ionomer cement composition of this invention can be said to show so much sharpness at initial setting, to be much less sensitive to water at the early stage of setting and thus stable in the oral cavity.

EXAMPLE 5

Sufficiently mixed together were 20 g of aluminium oxide, 43 g of silicic anhydride, 15 g of calcium fluoride, 8 g of calcium phosphate and 14 g of strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. Added to 100 g of the glass powders were 1.0 g of benzyl diethyl ketal, 0.1 g of 1-chloroanthraquinone and 0.5 g of dimethylaminoethyl methacrylate, and they were well-mixed together with a mortar in a dark room to prepare cement powders. On the other hand, 30 g of polyacrylic acid having an average molecular weight of 12,000, 30 g of methylene-bis-2-methacryloxyethyl-4-cyclohexyl carbamate, 40 g of distilled water, 1.5 g of polyoxyethylene sorbitol monolaurate and 0.5 g of decaglycerin monostearate ester were mixed under agitation for 60 minutes into a homogeneous state to prepare an aqueous cement solution. 2.6 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 23 Hv in measurement. A compressive strength showed 150 MPa after one day. To put it another way, the glass ionomer cement composition of this invention can be said to show so much sharpness at initial setting, to be much less sensitive to water at the early stage of setting and thus stable in the oral cavity.

EXAMPLE 6

Sufficiently mixed together were 20 g of aluminium oxide, 43 g of silicic anhydride, 15 g of calcium fluoride, 8 g of calcium phosphate and 14 g of strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. Well-mixed with 100 g of the glass powders were 20 g of a 10% solution of γ-methacryloxypropyltrimethoxysilane in ethanol in a mortar to treat them with the silane by drying at 110° C. for 2 hours with a steam dryer. Well-mixed with 100 g of the silane-treated powders were 0.5 g of camphor quinone and 1.0 g of dimethylaminoethyl methacrylate, and they were well-mixed together with a mortar in a dark room to prepare cement powders. On the other hand, 25 g of polyacrylic acid having an average molecular weight of 20,000, 10 g of polymaleic acid having an average molecular weight of 7000, 30 g of 2,2'-bis[3(4-phenoxy)-2-hydroxypropane-1-methacrylate]propane, 35 g of distilled water, 1.5 g of decaglycerin monolinoleate ester and 0.5 g of decaglycerin mono-isostearate ester were mixed under agitation for 60 minutes into a homogeneous state to prepare an aqueous cement solution. 2.6 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface was showed a cured state, and its contact with water indicated no dissolution. At the time when 5 minutes elapsed after the initiation of mixing, a Vickers surface hardness showed 26 Hv in measurement. A compressive strength showed 162 MPa after one day. To put it another way, the glass ionomer cement composition of this invention can be said to show so much sharpness at initial setting, to be much less sensitive to water at the early stage of setting and thus stable in the oral cavity.

EXAMPLE 7

Sufficiently mixed together were 20 g of aluminium oxide, 43 g of silicic anhydride, 15 g of calcium fluoride, 8 g of calcium phosphate and 14 g of strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. Well-mixed with 100 g of the glass powders were 20 g of a 10% solution of vinyltriethoxysilane in ethanol in a mortar to treat them with the silane by drying at 110° C. for 2 hours with a steam dryer. Well-mixed with 100 g of the silane-treated powders were 1.0 g of benzoin ethyl ether and 1.0 g of dimethylaminoethyl methacrylate, and they were well-mixed together with a mortar in a dark room to prepare cement powders. On the other hand, 30 g of a acrylic acid/itaconic acid copolymer having an average molecular weight of 18,000, 30 g of 2,2'-bis[3(4-phenoxy)-2-hydroxypropane-1-methacrylate]propane, 10 g of di-2-methacryloxyethyl-tetramethylene dicarbamate, 30 g of distilled water, 1.5 g of polyoxyethylene sorbitan mono-oleic acid ester and 0.5 g of polyoxyethylene glycerin monostearate ester were mixed under agitation for 60 minutes into a homogeneous state to prepare an aqueous cement solution. 2.6 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 24 Hv in measurement. A compressive strength showed 150 MPa after one day. To put it another way, the glass ionomer cement composition of this invention can be said to show so much sharpness at initial setting, to be much less sensitive to water at the early stage of setting and thus stable in the oral cavity.

EXAMPLE 8

Sufficiently mixed together were 20 g of aluminium oxide, 45 g of silicic anhydride, 10 g of calcium fluoride, 5 g of calcium phosphate and 15 g of strontium carbonate, which were then melted by retaining them for 5 hours in a high-temperature electric furnace of 1150° C. After melting, the glass melt is cooled down, ground for 12 hours with a ball mill and passed through a 200-mesh sieve (ASTM) to prepare glass powders. Well-mixed with 100 g of the glass powders were 20 g of a 10% solution of vinyl-tris(β-methoxyethoxy)silane in methanol in a mortar to treat them with the silane by drying at 110° C. for 2 hours with a steam dryer. Well-mixed with 100 g of the silane-treated powders were 0.5 g of camphor quinone, 1.0 g of benzoyl peroxide and 1.0 g of triethylamine, and they were well-mixed together with a mortar in a dark room to prepare cement powders. On the other hand, 20 g of an acrylic acid/maleic acid copolymer having an average molecular weight of 20,000, 50 g of di-1-methyl-2-methacryloxyethyl-hexamethylene dicarbamate, 30 g of distilled water, 1.9 g of isopropyl myristate and 0.1 g of polyoxyethylene polyoxypropylenecetyl ether were mixed under agitation for 60 minutes into a homogeneous state to prepare an aqueous cement solution. 2.6 g of the cement powders was mixed with 1.0 g of the cement liquid for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 24 Hv in measurement. A compressive strength showed 160 MPa after one day. To put it another way, the glass ionomer cement composition of this invention can be said to show so much sharpness at initial setting, to be much less sensitive to water at the early stage of setting and thus stable in the oral cavity.

EXAMPLE 9

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Well-mixed under agitation with 100 g of the glass powders were 30 g of a 3% aqueous solution of carboxymethyl cellulose to prepare a paste A. On the other hand, 20 g of an acrylic acid having an average molecular weight of 12,000, 70 g of di-2-methacryloxyethyl-hexamethylene dicarbamate, 10 g of distilled water, 1.0 g of camphor quinone and 10 g of finely ground silica having a mean particle size of 0.05 μm were mixed under agitation for 60 minutes into a homogeneous state to prepare a paste B. 1.0 g of the paste A was mixed with 1.0 g of the paste B for 30 seconds. After 60 seconds of the initiation of mixing, the product was exposed to light from a visible light irradiator Luxor (made by I.C.I., England) having a tungsten halogen lamp for 30 seconds to cure the glass ionomer cement. The surface showed a cured state, and its contact with water indicated no dissolution. At the time when 5 minutes elapsed after the initiation of mixing, a Vickers surface hardness was 20 Hv, as determined. A compressive strength showed 141 MPa in measurement after one day. To put it another way, the glass ionomer cement composition of this invention can be said to show so much sharpness at initial setting, to be much less sensitive to water at the early stage of setting and thus stable in the oral cavity.

EXAMPLE 10

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 100 g of the glass powders were 28 g of a 5% aqueous solution of polyvinyl alcohol, 0.5 g of camphor quinone and 1.0 g of dimethylaminoethyl methacrylate, and they were well-mixed together in a dark room with a mortar to prepare a paste A. On the other hand, 25 g of a polyacrylic acid having an average molecular weight of 20,000, 5 g of tartaric acid, 20 g of di-2-methacryloxyethyl-hexamethylene dicarbamate, 50 g of distilled water and 3 g of polyethylene glycol laurate were mixed under agitation for 60 minutes into a homogeneous state to prepare an aqueous cement solution. 3.0 g of the paste A was mixed with 1.0 g of the cement liquid for 30 seconds. After 60 seconds of the initiation of mixing, the product was exposed to light from a visible light irradiator Luxor (made by I.C.I., England) having a tungsten halogen lamp for 30 seconds to cure the glass ionomer cement. The surface showed a cured state, and its contact with water indicated no dissolution. At the time when 5 minutes elapsed after the initiation of mixing, a Vickers surface hardness showed 20 Hv in measurement. A compressive strength showed 135 MPa after one day. To put it another way, the glass ionomer cement composition of this invention can be said to show so much sharpness at initial setting, to be much less sensitive to water at the early stage of setting and thus stable in the oral cavity.

EXAMPLE 11

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 70 g of the glass powders were 30 g of di-2-methacryloxyethyl-hexamethylene carbamate, 2 g of sorbitan monooleic acid ester, 0.2 g of 1,2-benzanthraquinone and 0.5 g of dimethylaminoethyl methacrylate, and they were well-mixed together in a dark room with a mortar to prepare a paste A. On the other hand, 60 g of a polyacrylic acid having an average molecular weight of 40,000, 40 g of distilled water, 0.2 g of polyoxyethylene sorbitol monolaurate and 1.0 g of benzyl dimethyl ketal were mixed under agitation for 60 minutes into a homogeneous state to prepare a paste B. 1.5 g of the paste A was mixed with 1.0 g of the paste B for 30 seconds. After 60 seconds of the initiation of mixing, the product was exposed to light from a visible light irradiator Luxor (made by I.C.I., England) having a tungsten halogen lamp for 30 seconds to cure the glass ionomer cement. The surface showed a cured state, and its contact with water indicated no dissolution. At the time when 5 minutes elapsed after the initiation of mixing, a Vickers surface hardness showed 22 Hv in measurement. A compressive strength showed 135 MPa after one day. To put it another way, the glass ionomer cement composition of this invention can be said to show so much sharpness at initial setting, to be much less sensitive to water at the early stage of setting and thus stable in the oral cavity.

EXAMPLE 12

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. Added to 75 g of the glass powders were 10 g of di-1-methyl-2-methacryloxyethyl-trimethyl dicarbamate, 15 g of a 10% aqueous solution of polyvinylpyrrolidone, 1.0 g of polyoxyethylene sorbitol monolaurate, 0.5 g of decaglycerin monostearate and 0.5 g of 4-dimethylaminoisoamyl benzoate, and they were well-mixed together in a dark room with a mortar to prepare a paste A. To prepare a paste B, on the other hand, homogeneously mixed under agitation for 60 minutes were 30 g of a polyacrylic acid having an average molecular weight of 40,000, 50 g of di-1-methyl-2-methacryloxyethyl-trimethylhexamethylene dicarbamate, 20 g of distilled water, 0.5 g of camphor quinone, 0.5 g of benzoyl peroxide, 1.0 g of polyoxyethylene sorbitol monolaurate and 0.2 g of decaglycerin monostearate. 2.5 g of the paste A was mixed with 1.0 g of the paste B for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 23 Hv in measurement. A compressive strength showed 135 MPa after one day. To put it another way, the glass ionomer cement composition of this invention can be said to show so much sharpness at initial setting, to be much less sensitive to water at the early stage of setting and thus stable in the oral cavity.

EXAMPLE 13

Sufficiently mixed together were 20 g of aluminium oxide, 43 g of silicic anhydride, 15 g of calcium fluoride, 8 g of calcium phosphate and 14 g strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. Added to 75 g of the glass powders were 10 g of di-2-methacryloxyethyl-trimethylhexamethylene dicarbamate, 15 g of methylene-bis-2-methacryloxyethyl-4-cyclohexyl carbamate, 1.5 g of polyoxyethylene sorbitol monolaurate, 0.5 g of decaglycerin monostearate and 0.5 g of dimethylaminoethyl methacrylate, and they were well-mixed with a mortar to prepare a paste A. On the other hand, 100 g of soda feltspar powders were treated with 2 g of vinyltris($\beta$-methoxyethoxy)silane. Added to 50 g of the silane treated soda feltspar powders were 30 g of a polymaleic acid having an average molecular weight of 7000, 20 g of distilled water, 1.0 g of benzyl diethyl ketal and 0.1 g of 1-chloroanthraquinone, and they were well-mixed together in a dark room into a homogeneous state, thereby preparing a paste B. 2.0 g of the paste A was mixed with 1.0 g of the paste B for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 21 Hv in measurement. A compressive strength showed 141 MPa after one day. To put it another way, the glass ionomer cement composition of this invention can be said to show so much sharpness at initial setting, to be much less sensitive to water at the early stage of setting and thus stable in the oral cavity.

EXAMPLE 14

Sufficiently mixed together were 20 g of aluminium oxide, 43 g of silicic anhydride, 15 g of calcium fluoride, 8 g of calcium phosphate and 14 g of strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. After 100 g of the glass powders had been well-mixed with 20 g of a 10% solution of $\gamma$-methacryloxypropyltrimethoxysilane in ethanol in a mortar, the mixture was dried at 110° C. for 2 hours with a steam dryer to prepare silane-treated powders. Mixed with 76 g of the silane-treated powders were 10 g of 2,2'-bis[3(4-phenoxy)-2-hydroxypropane-1-methacrylate]propane, 14 g of di-2-methacryloxyethylhexamethylene dicarbamate and 1.0 g of dimethylaminoethyl methacrylate, and they were then well-mixed together in a dark room with a mortar to prepare a paste A. On the other hand, 100 g of finely ground silica were sufficiently mixed with 30 g of a 10% solution of $\gamma$-methacryloxypropyltrimethoxysilane in ethanol and the mixture was thereafter dried at 110° C. for 2 hours with a steam dryer to prepare silane-treated silica powders. 50 g of the silane-treated silica powders, 15 g of a polyacrylic acid having an average molecular weight of 20,000, 5 g of a polymaleic acid having an average molecular weight of 7000, 30 g of distilled water and 0.5 g of camphor quinone were mixed together under agitation for 60 seconds into a homogeneous state, thereby preparing a paste B. 2.0 g of the paste A was mixed with 1.0 g of the paste B for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 23 Hv in measurement. A compressive strength showed 150 MPa after one day. To put it another way, the glass ionomer cement composition of this invention can be said to show so much sharpness at initial setting, to be much less sensitive to water at an early stage of setting and thus to be stable material in the oral cavity.

EXAMPLE 15

Sufficiently mixed together were 20 g of aluminium oxide, 43 g of silicic anhydride, 15 g of calcium fluoride, 8 g of calcium phosphate and 14 g of strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. Well-mixed with 100 g of the glass powders were 20 g of a 10% solution of vinyltriethoxysilane in ethanol in a mortar to treat them with the silane by drying at 110° C. for 2 hours with a steam dryer. Well-mixed with 75 g of the silane-treated powders were 10 g of 2,2'-bis[3(4-phenoxy)-2-hydroxypropane-1-methacrylate]propane, 10 g of di-2-methacryloxyethyl-1-tetramethylene dicarbamate, 5 g of a polyacrylic acid having a mean molecular weight of 12,000, 1.0 g of benzoin ethyl ether, 1.0 g of benzoyl peroxide and 1.0 g of dimethylaminoethyl methacrylate in a dark room with a mortar to prepare a paste A. On the other hand, 30 g of an acrylic acid/itaconic acid copolymer having an average molecular weight of 18,000, 20 g of 2,2'-bis[3(4-phenoxy)-2-hydroxypropane-1-methacrylate]propane, 20 g of di-2-methacryloxyethyl-tetramethylene dicarbamate, 20 g of distilled water, 10 g of finely ground silica, 1.0 g of polyoxyethylene sorbitol mono-oleic acid ester and 0.2 g of polyoxyethylene glycerin monostearate were mixed under agitation for 60 seconds into a homogeneous state to prepare a paste B. 2.0 g of the paste A was mixed with 1.0 g of the paste B for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 23 Hv in measurement. A compressive strength showed 144 MPa after one day. To put it another way, the glass ionomer cement composition of this invention can be said to show so much sharpness at initial setting, to be much less sensitive to water at an early stage of setting and thus to be stable material in the oral cavity.

EXAMPLE 16

Sufficiently mixed together were 20 g of aluminium oxide, 45 g of silicic anhydride, 10 g of calcium fluoride, 5 g of calcium phosphate and 15 g of strontium carbonate, which were then melted by retaining them for 5 hours in a high-temperature electric furnace of 1150° C. After melting, the glass melt is cooled down, ground for 12 hours with a ball mill and passed through a 200-mesh sieve (ASTM) to prepare glass powders. Well-mixed under agitation with 100 g of the glass powders were 20 g of a 10% solution of vinyl-tris($\beta$-methoxyethoxy)silane in ethanol to treat them with the silane by drying at 110° C. for 2 hours with a steam dryer. Well-mixed with 50 g of the silane-treated powders were 30 g of di-1-methyl-2-methacryloxyethylhexamethylene dicarbamate, 20 g of an acrylic acid/maleic acid copolymer having an average molecular weight of 20,000, 0.5 g of camphor quinone, 1.0 g of benzoyl peroxide and 1.0 g of triethylamine in a dark room with a mortar to prepare a paste A. On the other hand, 70 g of an acrylic acid/maleic acid copolymer having an average molecular weight of 18,000, 30 g of distilled water, 0.9 g of isopropyl myristate and 0.1 g of polyoxyethylene polyoxypropylene cetyl ether were mixed under agitation for 60 minutes into a homogeneous state to prepare a paste B. 2.0 g of the paste A was mixed with 1.0 g of the paste B for 30 seconds. After 60 seconds of the initiation of mixing, the product was exposed to light from a visible light irradiator Luxor (made by I.C.I., England) having a tungusten halogen lamp for 30 seconds to cure the glass ionomer cement. The surface showed a cured state, and its contact with water indicated no dissolution. At the time when 5 minutes elapsed after the initiation of mixing, a Vickers surface hardness showed 22 Hv in measurement. A compressive strength showed 158 MPa after one day. To put it another way, the glass ionomer cement composition of this invention can be said to show so much sharpness at initial setting, to be much less sensitive to water at an early stage of setting and thus to be stable material in the oral cavity.

COMPARATIVE EXAMPLE 1

Sufficiently mixed together were 21 g of aluminium oxide, 45 g of silicic anhydride, 12 g of calcium fluoride, 10 g of calcium phosphate and 12 g of calcium carbonate, which were then melted by retaining them for 5 hours in a high-temperature electric furnace of 1100° C. After melting, the glass melt is cooled down, ground for 10 hours with a ball mill and passed through a 200-mesh sieve (ASTM) to prepare glass powders. On the other hand, a 50% aqueous solution of a polyacrylic acid having an average molecular weight of 20,000 was prepared in the form of a cement liquid. 2.5 g of the cement powders was mixed with 1.0 g of the cement liquid for 30 seconds. Even at the time when 2 minutes elapsed after the initiation of mixing, the surface was not hardened and, upon being contacted with water, dissolved. After five minutes of the initiation of mixing, any Vickers surface hardness could not be determined. A compressive strength showed 135 MPa after one day.

COMPARATIVE EXAMPLE 2

Sufficiently mixed together were 20 g of aluminium oxide, 45 g of silicic anhydride, 10 g of calcium fluoride, 5 g of sodium fluoride, 5 g of calcium phosphate and 15 g of strontium carbonate, which were then melted by retaining them for 5 hours in a high-temperature electric furnace of 1150° C. After melting, the glass melt is cooled down, ground for 12 hours with a ball mill and passed through a 200-mesh sieve (ASTM) to prepare glass powders. On the other hand, an aqueous solution consisting of 40 g of an acrylic acid/maleic acid copolymer having an average molecular weight of 18,000, 10 g of tartaric acid and 50 g of distilled water was prepared in the form of a cement liquid. 2.6 g of the cement powders was mixed with 1.0 g of the cement liquid for 30 seconds. At the time when 2 minutes elapsed after the initiation of mixing, the surface dissolved upon brought into contact with water. Even when 5 minutes elapsed after the initiation of mixing, any Vickers surface hardness could not be measured. It is noted that a compressive strength showed 135 MPa after one day.

COMPARATIVE EXAMPLE 3

Sufficiently mixed together were 20 g of aluminium oxide, 43 g of silicic anhydride, 15 g of calcium fluoride, 8 g of calcium phosphate and 14 g of strontium carbonate, which were then melted by retaining them for 5 hours in a high-temperature electric furnace of 1200° C. After melting, the glass melt is cooled down, ground for 12 hours with a ball mill and passed through a 200-mesh sieve (ASTM) to prepare glass powders. On the other hand, 40 g of an acrylic acid/itaconic acid copolymer having an average molecular weight of 18,000, 10 g of tartaric acid and 50 g of distilled water were uniformly mixed together into a cement liquid. 2.5 g of the cement powders was mixed with 1.0 g of the cement liquid for 30 seconds. Even when about 2 minutes elapsed after the initiation of mixing, the surface was not cured and, upon in contact with distilled water, dissolved. Even when 5 minutes elapsed after the initiation of mixing, the surface was not hardened and, upon in contact with distilled water, dissolved. Even when 5 minutes elapsed after the initiation of mixing, any Vickers surface hardness could not be measured. It is noted that a compressive strength showed 132 MPa after one day.

Compositions of the present invention undergo rapider initial setting reactions, are much less sensitive to water at the early stage of setting and much more reduced in the surface dissolution, when compared with conventional dental glass ionomer cements. They have some additional advantages of excelling in biocompatibility, adhesion to tooth substance, intra-mouth durability and translucency of their hardened masses which make them more agreeable to look at, and successfully solves the gravest problem of conventional glass ionomer cements that their setting reactions are prevented from proceeding upon in contact with moisture such as saliva with the resulting deteriorations of physical properties. Thus, it is unlikely that the present compositions may be either embrittled or clouded on their surfaces even upon comining into contact with water at the initial stage of curing or deteriorated in terms of strength, giving hardened masses more agreeable to look at.

What is claimed is:

1. A dental glass ionomer cement composition consisting essentially of:
   (a) a polymer of an α-β unsaturated carboxylic acid having a weight average molecular weight of 5,000 to 40,000,
   (b) a fluoroaluminosilicate glass powder having an average particle size of 0.02 to 10 μm and a specific gravity of 2.4 to 4.0 and capable of reacting with said "polymer of an α-β unsaturated carboxylic acid having a weight average molecular weight of 5,000 to 40,000",
   (c) a polymerizable unsaturated organic compound having at least one $CH_2=C(R1)-COO-$ group wherein R1=H or $CH_3$,
   (d) a polymerization catalyst,
   (e) water,
   (f) a surface active agent, and
   (g) a reducing agent.

2. A dental glass ionomer cement composition as claimed in claim 1, wherein said "(c) polymerizable unsaturated organic compound having at least one $CH_2=C(R1)-COO-$ group wherein R1=H or $CH_3$" undergoes no reaction with said "fluoroaluminosilicate glass powder having an average particle size of 0.02 to 10 μm and a specific gravity of 2.4 to 4.0 and capable of reacting with said "polymer of an α-β unsaturated carboxylic acid having a weight average molecular weight of 5,000 to 40,000"".

3. A dental glass ionomer cement composition consisting essentially of:
   (a) 5 to 100 parts by weight of a polymer of an α-β unsaturated carboxylic acid having a weight average molecular weight of 5,000 to 40,000,
   (b) 5 to 100 parts by weight of a fluoroaluminosilicate glass powder having an average particle size of 0.02 to 10 μm and a specific gravity of 2.4 to 4.0 and capable of reacting with said "polymer of an α-β unsaturated carboxylic acid having a weight average molecular weight of 5,000 to 40,000",
   (c) 5 to 100 parts by weight of a polymerizable unsaturated organic compound having at least one $CH_2=C(R1)-COO-$ group wherein R1=H or $CH_3$,
   (d) 0.01 to 5 parts by weight of a polymerization catalyst,
   (e) 2 to 50 parts by weight of water,
   (f) 0.01 to 20 parts by weight of a surface active agent, and
   (g) 0.01 to 5 parts by weight of a reducing agent.

4. A dental glass ionomer cement composition as claimed in any one of claims 1 to 3, wherein said "polymer of an α-β unsaturated carboxylic acid having a weight average molecular weight of 5,000 to 40,000" is a co- or homo-polymer containing at least one selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid.

5. A dental glass ionomer cement composition as claimed in any one of claims 1 to 4, wherein said "polymer of an α-β unsaturated carboxylic acid having a weight average molecular weight of 5,000 to 40,000" is a co- or homo-polymer containing acrylic and maleic acids.

6. A dental glass ionomer cement composition as claimed in any one of claims 1 to 5, wherein said "polymerizable unsaturated organic compound having at least one $CH_2=C(R1)-COO-$ group wherein R1=H or $CH_3$" is an ester of acrylic or methacrylic acid.

7. A dental glass ionomer cement composition as claimed in any one of claims 1 to 6, wherein said "fluoroaluminosilicate glass powder having an average particle size of 0.02 to 10 μm and a specific gravity of 2.4 to 4.0 and capable of reacting with said "polymer of an α-β unsaturated carboxylic acid having a weight average molecular weight of 5,000 to 40,000"" contains $Al^{3+}$, $Si^{4+}$, $F^-$ and $O^{2-}$ as main components and including further $Sr^{2+}$ and/or $Ca^{2+}$.

8. A dental glass ionomer cement composition as claimed in any one of claims 1 to 7, wherein said "polymerization catalyst" is a photopolymerization catalyst.

9. A dental glass ionomer cement composition as claimed in any one of claims 1 to 8, wherein said "fluoroaluminosilicate glass powder having an average particle size of 0.02 to 10 μm and a specific gravity of 2.4 to 4.0 and capable of reacting with said "polymer of an α-β unsaturated carboxylic acid having a weight average molecular weight of 5,000 to 40,000" is a fluoroaluminosilicate glass powder which is coated on its surface with an organic compound having a polymerizable, ethylenically unsaturated double bond in a quantity of 0.01 to 20 parts by weight with respect to 100 parts by weight of said powder, and in which said polymerizable, ethylenically unsaturated double bond remains.

10. A dental glass ionomer cement composition as claimed in any one of claims 1 to 9, which additionally includes:
    h. 0 to 50 parts by weight of an inorganic filler having an average particle size of 0.02 to 10 μm and undergoing no reaction with said "polymer of an α-β unsaturated carboxylic acid having a weight average molecular weight of 5,000 to 40,000".

11. A dental glass ionomer cement composition as claimed in claim 10, wherein said "h. inorganic filler having an average particle size of 0.02 to 10 μm and undergoing no reaction with said "polymer of an α-β unsaturated carboxylic acid having a weight average molecular weight of 5,000 to 40,000"" is an inorganic filler which is coated on its surface with an organic compound having a polymerizable, ethylenically unsaturated double bond in a quantity of 0.01 to 20 parts by weight with respect to 100 parts by weight of said glass powder, and in which said polymerizable, ethylenically unsaturated double bond remains.

12. A dental glass ionomer cement composition as claimed in any one of claims 1 to 11, which comprises formulations A and B, each being a paste having a viscosity of 2,000 cP or higher.

13. A dental glass ionomer cement composition as claimed in claim 12, which additionally include:
    i. 0 to 20 parts by weight of a water-soluble high-molecular substance.

* * * * *